(12) United States Patent
Nita

(10) Patent No.: US 10,835,267 B2
(45) Date of Patent: *Nov. 17, 2020

(54) ULTRASOUND CATHETER HAVING PROTECTIVE FEATURE AGAINST BREAKAGE

(71) Applicant: Flowcardia, Inc., Franklin Lakes, NJ (US)

(72) Inventor: Henry Nita, Redwood City, CA (US)

(73) Assignee: Flowcardia, Inc., Franklin Lakes, NJ (US)

(*) Notice: Subject to any disclaimer, the term of this patent is extended or adjusted under 35 U.S.C. 154(b) by 337 days.

This patent is subject to a terminal disclaimer.

(21) Appl. No.: 15/791,074

(22) Filed: Oct. 23, 2017

(65) Prior Publication Data

US 2018/0042636 A1 Feb. 15, 2018

Related U.S. Application Data

(63) Continuation of application No. 13/919,739, filed on Jun. 17, 2013, now Pat. No. 9,955,994, which is a
(Continued)

(51) Int. Cl.
*A61B 17/22* (2006.01)
*A61M 25/00* (2006.01)
(Continued)

(52) U.S. Cl.
CPC ... *A61B 17/22012* (2013.01); *A61M 25/0068* (2013.01); *A61M 25/0069* (2013.01);
(Continued)

(58) Field of Classification Search
CPC ...... A61B 17/320068; A61B 17/22012; A61B 2017/22014; A61B 2017/22039;
(Continued)

(56) References Cited

U.S. PATENT DOCUMENTS 3,296,620 A 1/1967 Rodda
3,433,226 A 3/1969 Boyd
(Continued)

FOREIGN PATENT DOCUMENTS

AU 2007240154 A1 1/2008
DE 2438648 A1 2/1976
(Continued)

OTHER PUBLICATIONS

Japanese Office Action for Japanese Application No. 2010-134566, dated Mar. 2, 2012.
(Continued)

*Primary Examiner* — Katrina M Stransky

(57) ABSTRACT

An ultrasound catheter has an elongate flexible catheter body having a lumen extending longitudinally therethrough, and an ultrasound transmission member extending longitudinally through the lumen of the catheter body. The ultrasound transmission member has a proximal end that is coupled to a separate ultrasound generating device, and a distal tip that is attached to the distal end of the ultrasound transmission member and which is located at the distal end of the catheter body. The ultrasound transmission member is directly attached to the catheter body and/or to a guidewire tube either directly or via an attachment device. The catheter has an additional radiopaque marker positioned on the distal end the catheter.

17 Claims, 9 Drawing Sheets

Related U.S. Application Data continuation-in-part of application No. 12/004,984, filed on Dec. 21, 2007, now Pat. No. 8,496,669, which is a continuation-in-part of application No. 11/594,663, filed on Nov. 7, 2006, now Pat. No. 8,133,236, said application No. 13/919,739 is a continuation-in-part of application No. 11/879,170, filed on Jul. 16, 2007, now Pat. No. 8,506,519, which is a continuation-in-part of application No. 11/711,970, filed on Feb. 27, 2007, now abandoned, which is a continuation of application No. 10/601,245, filed on Jun. 20, 2003, now abandoned, which is a continuation-in-part of application No. 10/211,418, filed on Aug. 2, 2002, now Pat. No. 6,855,123, said application No. 11/711,970 is a continuation-in-part of application No. 10/251,227, filed on Sep. 20, 2002, now Pat. No. 6,702,748.

(51) Int. Cl.
  *A61B 17/32* (2006.01)
  *A61M 25/01* (2006.01)
  *A61M 25/09* (2006.01)
  *A61B 90/00* (2016.01)

(52) U.S. Cl.
  CPC ............... *A61M 25/0082* (2013.01); *A61B 2017/22014* (2013.01); *A61B 2017/22038* (2013.01); *A61B 2017/22039* (2013.01); *A61B 2017/320069* (2017.08); *A61B 2090/3966* (2016.02); *A61M 25/0108* (2013.01); *A61M 2025/0183* (2013.01); *A61M 2025/09166* (2013.01)

(58) Field of Classification Search
  CPC .... A61B 2017/22038; A61B 17/22004; A61B 17/22; A61B 17/2202; A61B 2017/22007; A61B 2017/320069; A61B 2017/320073; A61B 2017/22012; A61B 2017/22017; A61M 25/0069; A61M 25/0068; A61M 25/0082; A61M 25/0108
  See application file for complete search history.

(56) References Cited

U.S. PATENT DOCUMENTS

| | | |
|---|---|---|
| 3,443,226 A | 5/1969 | Knight |
| 3,565,062 A | 2/1971 | Kurls |
| 3,585,082 A | 6/1971 | Siller |
| 3,612,038 A | 10/1971 | Halligan |
| 3,631,848 A | 1/1972 | Muller |
| 3,679,378 A | 7/1972 | Van Impe et al. |
| 3,719,737 A | 3/1973 | Vaillancourt et al. |
| 3,739,460 A | 6/1973 | Addis et al. |
| 3,754,746 A | 8/1973 | Thiele |
| 3,823,717 A | 7/1974 | Pohlman et al. |
| 3,835,690 A | 9/1974 | Leonhardt et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance et al. |
| 4,417,578 A | 11/1983 | Banko |
| 4,425,115 A | 1/1984 | Wuchinich |
| 4,453,935 A | 6/1984 | Newton |
| 4,486,680 A | 12/1984 | Bonnet et al. |
| 44,495,232 | 1/1985 | Bauser et al. |
| 4,505,767 A | 3/1985 | Quin |
| 4,535,759 A | 8/1985 | Polk et al. |
| 4,545,767 A | 10/1985 | Suzuki et al. |
| 4,565,589 A | 1/1986 | Harrison |
| 4,565,787 A | 1/1986 | Bossle et al. |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,781,186 A | 11/1988 | Simpson et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 4,979,952 A | 12/1990 | Kubota et al. |
| 5,000,185 A | 3/1991 | Yock |
| 5,015,227 A | 5/1991 | Broadwin et al. |
| 5,026,384 A | 6/1991 | Farr et al. |
| 5,030,201 A | 7/1991 | Palestrant |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai et al. |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,131,393 A | 7/1992 | Ishiguro et al. |
| 5,156,143 A | 10/1992 | Bocquet et al. |
| 5,163,421 A | 11/1992 | Bernstein et al. |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,217,565 A | 6/1993 | Kou et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,236,414 A | 8/1993 | Takasu |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,279,546 A | 1/1994 | Mische et al. |
| 5,287,858 A | 2/1994 | Hammerslag et al. |
| 5,290,229 A | 3/1994 | Paskar |
| 5,304,115 A | 4/1994 | Pflueger et al. |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'Neill et al. |
| 5,325,860 A | 7/1994 | Seward et al. |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |

(56) References Cited

U.S. PATENT DOCUMENTS

| | | |
|---|---|---|
| 5,362,309 A | 11/1994 | Carter |
| 5,368,557 A | 11/1994 | Nita |
| 5,368,558 A | 11/1994 | Nita et al. |
| 5,376,084 A | 12/1994 | Bacich et al. |
| 5,378,234 A | 1/1995 | Hammerslag et al. |
| 5,380,274 A * | 1/1995 | Nita .................. A61B 17/22012 604/22 |
| 5,380,316 A | 1/1995 | Aita et al. |
| 5,382,228 A * | 1/1995 | Nita .................. A61B 17/22012 604/22 |
| 5,383,460 A | 1/1995 | Jang et al. |
| 5,389,096 A | 2/1995 | Aita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,403,324 A | 4/1995 | Ciervo et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,449,370 A | 9/1995 | Vaitekunas |
| 5,451,209 A | 9/1995 | Ainsworth et al. |
| 5,462,529 A | 10/1995 | Simpson et al. |
| 5,465,733 A | 11/1995 | Hinohara et al. |
| 5,474,530 A | 12/1995 | Passafaro et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,498,236 A | 3/1996 | Dubrul et al. |
| 5,507,738 A | 4/1996 | Ciervo |
| 5,516,043 A | 5/1996 | Manna et al. |
| 5,527,273 A | 6/1996 | Manna et al. |
| 5,538,512 A | 7/1996 | Zenzon et al. |
| 5,540,656 A | 7/1996 | Pflueger et al. |
| 5,542,917 A | 8/1996 | Nita et al. |
| 5,597,497 A | 1/1997 | Dean et al. |
| 5,597,882 A | 1/1997 | Schiller et al. |
| 5,607,421 A | 3/1997 | Jeevanandam et al. |
| 5,611,807 A | 3/1997 | O'Boyle |
| 5,618,266 A | 4/1997 | Liprie |
| 5,626,593 A | 5/1997 | Imran |
| 5,627,365 A | 5/1997 | Chiba et al. |
| 5,649,935 A | 7/1997 | Kremer et al. |
| 5,658,282 A | 8/1997 | Daw et al. |
| 5,665,062 A | 9/1997 | Houser |
| 5,685,841 A | 11/1997 | Mackool |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,725,494 A | 3/1998 | Brisken |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,127 A | 11/1998 | DeCastro |
| 5,830,222 A | 11/1998 | Makower |
| 5,846,218 A | 12/1998 | Brisken et al. |
| 5,873,835 A | 2/1999 | Hastings et al. |
| 5,876,385 A | 3/1999 | Ikari et al. |
| 5,893,838 A | 4/1999 | Daoud et al. |
| 5,895,397 A | 4/1999 | Jang et al. |
| 5,902,287 A | 5/1999 | Martin |
| 5,904,667 A | 5/1999 | Falwell |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck et al. |
| 6,004,335 A | 12/1999 | Vaitekunas et al. |
| 6,007,499 A | 12/1999 | Martin et al. |
| 6,007,514 A * | 12/1999 | Nita .................. A61B 17/22012 604/22 |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud |
| 6,036,689 A | 3/2000 | Tu et al. |
| 6,051,010 A | 4/2000 | DiMatteo et al. |
| 6,066,135 A | 5/2000 | Honda |
| 6,113,558 A | 9/2000 | Rosenschein et al. |
| 6,120,515 A | 9/2000 | Rogers et al. |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,159,187 A | 12/2000 | Park et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 | 4/2001 | Jerger et al. |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,241,744 B1 | 6/2001 | Imran et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,298,620 B1 | 10/2001 | Hatzinikolas |
| 6,302,875 B1 | 10/2001 | Makower et al. |
| 6,309,358 B1 | 10/2001 | Okubo |
| 6,315,741 B1 | 11/2001 | Martin et al. |
| 6,315,754 B1 | 11/2001 | Daoud et al. |
| 6,331,171 B1 | 12/2001 | Cohen |
| 6,346,192 B2 | 2/2002 | Buhr et al. |
| 6,379,378 B1 | 4/2002 | Werneth et al. |
| 6,387,109 B1 | 5/2002 | Davison et al. |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,737 B1 | 9/2002 | Nita et al. |
| 6,454,757 B1 | 9/2002 | Nita et al. |
| 6,454,997 B1 | 9/2002 | Divino, Jr. et al. |

(56) References Cited

U.S. PATENT DOCUMENTS

| | | |
|---|---|---|
| 6,484,052 B1 | 11/2002 | Visuri et al. |
| 6,491,707 B2 | 12/2002 | Makower et al. |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 | 1/2003 | Brennan et al. |
| 6,508,784 B1 | 1/2003 | Shu |
| 6,511,458 B2 | 1/2003 | Milo et al. |
| 6,514,249 B1 | 2/2003 | Maguire et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,547,788 B1 | 4/2003 | Maguire et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |
| 6,607,698 B1 | 8/2003 | Spears et al. |
| 6,610,077 B1 | 8/2003 | Hancock et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,814,727 B2 | 11/2004 | Mansouri-Ruiz |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,149,587 B2 | 12/2006 | Wardle et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,628,763 B2 | 12/2009 | Noriega et al. |
| 7,648,478 B2 | 1/2010 | Soltani et al. |
| 7,758,510 B2 | 7/2010 | Nita et al. |
| 7,771,358 B2 | 8/2010 | Moehring et al. |
| 7,771,452 B2 | 8/2010 | Pal et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,918,819 B2 | 4/2011 | Karmarkar et al. |
| 7,935,108 B2 | 5/2011 | Baxter et al. |
| 7,938,819 B2 | 5/2011 | Kugler et al. |
| 7,942,809 B2 | 5/2011 | Leban |
| 7,955,293 B2 | 6/2011 | Nita et al. |
| 7,993,308 B2 | 8/2011 | Rule et al. |
| 8,038,693 B2 | 10/2011 | Allen |
| 8,043,251 B2 | 10/2011 | Nita et al. |
| 8,052,607 B2 | 11/2011 | Byrd |
| 8,083,727 B2 | 12/2011 | Kugler et al. |
| 8,133,236 B2 | 3/2012 | Nita |
| 8,152,753 B2 | 4/2012 | Nita et al. |
| 8,172,758 B2 | 5/2012 | Harhen |
| 8,221,343 B2 | 7/2012 | Nita et al. |
| 8,226,566 B2 | 7/2012 | Nita |
| 8,246,643 B2 | 8/2012 | Nita |
| 8,257,378 B1 | 9/2012 | O'connor |
| 8,308,677 B2 | 11/2012 | Nita et al. |
| 8,343,134 B2 | 1/2013 | Kost et al. |
| 8,414,543 B2 | 4/2013 | Mcguckin, Jr. et al. |
| 8,496,669 B2 | 7/2013 | Nita et al. |
| 8,506,519 B2 | 8/2013 | Nita |
| 8,613,700 B2 | 12/2013 | Ueno et al. |
| 8,613,751 B2 | 12/2013 | Nita et al. |
| 8,617,096 B2 | 12/2013 | Nita et al. |
| 8,632,560 B2 | 1/2014 | Pal et al. |
| 8,641,630 B2 | 2/2014 | Nita et al. |
| 8,647,293 B2 | 2/2014 | Nita |
| 8,647,296 B2 | 2/2014 | Moberg et al. |
| 8,663,259 B2 | 3/2014 | Levine et al. |
| 8,668,709 B2 | 3/2014 | Nita et al. |
| 8,690,818 B2 | 4/2014 | Bennett et al. |
| 8,690,819 B2 | 4/2014 | Nita et al. |
| 8,702,595 B2 | 4/2014 | Ueki |
| 8,708,892 B2 | 4/2014 | Sugiyama et al. |
| 8,708,994 B2 | 4/2014 | Pettis et al. |
| 8,725,228 B2 | 5/2014 | Koblish et al. |
| 8,764,700 B2 | 7/2014 | Zhang et al. |
| 8,768,433 B2 | 7/2014 | Jenkins et al. |
| 8,790,291 B2 | 7/2014 | Nita et al. |
| 8,974,446 B2 | 3/2015 | Nguyen et al. |
| 8,978,478 B2 | 3/2015 | Ishioka |
| 9,101,387 B2 | 8/2015 | Plowe et al. |
| 9,107,590 B2 | 8/2015 | Hansmann et al. |
| 9,237,837 B2 | 1/2016 | Omoto et al. |
| 9,265,520 B2 | 2/2016 | Nita |
| 9,282,984 B2 | 3/2016 | Nita |
| 9,314,258 B2 | 4/2016 | Nita et al. |
| 9,381,027 B2 | 7/2016 | Nita et al. |
| 9,421,024 B2 | 8/2016 | Nita et al. |
| 9,433,433 B2 | 9/2016 | Nita et al. |
| 9,603,615 B2 | 3/2017 | Sarge |
| 9,770,250 B2 | 9/2017 | Nita et al. |
| 9,955,994 B2 * | 5/2018 | Nita ............... A61B 17/22012 |
| 10,004,520 B2 | 6/2018 | Nita et al. |
| 2002/0022858 A1 | 2/2002 | Demond et al. |
| 2002/0049409 A1 | 4/2002 | Noda et al. |
| 2002/0077550 A1 | 6/2002 | Rabiner et al. |
| 2002/0188276 A1 | 12/2002 | Evans et al. |
| 2002/0189357 A1 | 12/2002 | Lai et al. |

(56) References Cited

U.S. PATENT DOCUMENTS

| | | |
|---|---|---|
| 2003/0009153 A1 | 1/2003 | Brisken et al. |
| 2003/0036705 A1 | 2/2003 | Hare et al. |
| 2003/0040762 A1 | 2/2003 | Dorros et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0019349 A1 | 1/2004 | Fuimaono et al. |
| 2004/0024393 A1 | 2/2004 | Nita et al. |
| 2004/0054367 A1 | 3/2004 | Teodoro, Jr. et al. |
| 2004/0138570 A1* | 7/2004 | Nita ............... A61B 17/22012 600/466 |
| 2004/0164030 A1 | 8/2004 | Lowe et al. |
| 2004/0167511 A1 | 8/2004 | Buehlmann et al. |
| 2004/0193033 A1 | 9/2004 | Badehi et al. |
| 2004/0204670 A1* | 10/2004 | Nita ............... A61B 17/22012 604/22 |
| 2005/0033311 A1 | 2/2005 | Guldfeldt et al. |
| 2005/0149110 A1 | 7/2005 | Wholey et al. |
| 2005/0165388 A1 | 7/2005 | Bhola |
| 2005/0171527 A1 | 8/2005 | Bhola |
| 2005/0228286 A1 | 10/2005 | Messerly et al. |
| 2006/0074441 A1 | 4/2006 | Mcguckin, Jr. et al. |
| 2006/0149169 A1 | 7/2006 | Nunomura et al. |
| 2006/0206039 A1 | 9/2006 | Wilson et al. |
| 2006/0264809 A1 | 11/2006 | Hansmann et al. |
| 2007/0016071 A1* | 1/2007 | Eberle ............... A61B 8/06 600/468 |
| 2007/0032749 A1 | 2/2007 | Overall et al. |
| 2007/0161945 A1 | 7/2007 | Nita et al. |
| 2007/0178768 A1 | 8/2007 | Harshman et al. |
| 2008/0033284 A1 | 2/2008 | Hauck |
| 2008/0071343 A1 | 3/2008 | Mayberry et al. |
| 2008/0108902 A1* | 5/2008 | Nita ............... A61B 17/22012 600/466 |
| 2008/0108937 A1* | 5/2008 | Nita ............... A61B 17/22012 604/22 |
| 2008/0208084 A1 | 8/2008 | Horzewski et al. |
| 2008/0221506 A1 | 9/2008 | Rodriguez et al. |
| 2008/0287804 A1* | 11/2008 | Nita ............... A61B 17/22012 600/466 |
| 2008/0294037 A1 | 11/2008 | Richter |
| 2009/0017293 A1 | 1/2009 | Arai et al. |
| 2009/0143795 A1 | 6/2009 | Robertson |
| 2010/0004558 A1 | 1/2010 | Frankhouser et al. |
| 2010/0023037 A1 | 1/2010 | Nita et al. |
| 2010/0069854 A1 | 3/2010 | Okoh et al. |
| 2010/0076454 A1 | 3/2010 | Bos |
| 2010/0121144 A1 | 5/2010 | Farhadi |
| 2010/0217306 A1 | 8/2010 | Raabe et al. |
| 2010/0268206 A1 | 10/2010 | Manwaring et al. |
| 2011/0046522 A1 | 2/2011 | Chan et al. |
| 2011/0105960 A1 | 5/2011 | Wallace |
| 2011/0130834 A1 | 6/2011 | Wilson et al. |
| 2011/0196399 A1 | 8/2011 | Robertson et al. |
| 2011/0196403 A1 | 8/2011 | Robertson et al. |
| 2011/0237982 A1 | 9/2011 | Wallace |
| 2011/0313328 A1 | 12/2011 | Nita |
| 2012/0010506 A1 | 1/2012 | Ullrich |
| 2012/0109021 A1 | 5/2012 | Hastings et al. |
| 2012/0130475 A1 | 5/2012 | Shaw |
| 2012/0217306 A1 | 8/2012 | Morrill Webb et al. |
| 2012/0238916 A1 | 9/2012 | Nita et al. |
| 2012/0238946 A1 | 9/2012 | Nita et al. |
| 2012/0311844 A1 | 12/2012 | Nita et al. |
| 2012/0330196 A1 | 12/2012 | Nita |
| 2013/0046297 A1 | 2/2013 | Lingeman et al. |
| 2013/0060169 A1 | 3/2013 | Yamada |
| 2013/0331652 A1 | 12/2013 | Okamoto |
| 2013/0338580 A1 | 12/2013 | Yamatani et al. |
| 2014/0005706 A1 | 1/2014 | Gelfand et al. |
| 2014/0012087 A1 | 1/2014 | Omoto |
| 2014/0039491 A1 | 2/2014 | Bakos et al. |
| 2014/0171804 A1 | 6/2014 | Van Hoven |
| 2014/0236118 A1 | 8/2014 | Unser et al. |
| 2014/0243712 A1 | 8/2014 | Humayun et al. |
| 2014/0350401 A1 | 11/2014 | Sinelnikov |
| 2014/0358028 A1 | 12/2014 | Vetter et al. |
| 2015/0025544 A1 | 1/2015 | Nita et al. |
| 2015/0073357 A1 | 3/2015 | Bagwell et al. |
| 2015/0105621 A1 | 4/2015 | Farhadi |
| 2015/0105715 A1 | 4/2015 | Pikus et al. |
| 2015/0133918 A1 | 5/2015 | Sachar |
| 2015/0148795 A1 | 5/2015 | Amos et al. |
| 2015/0157443 A1 | 6/2015 | Hauser et al. |
| 2015/0190660 A1 | 7/2015 | Sarge et al. |
| 2015/0297258 A1 | 10/2015 | Escudero et al. |
| 2015/0359651 A1 | 12/2015 | Wübbeling |
| 2016/0128717 A1 | 5/2016 | Nita |
| 2016/0135835 A1 | 5/2016 | Onuma |
| 2016/0183956 A1 | 6/2016 | Nita |
| 2016/0271362 A1 | 9/2016 | Van Liere |
| 2016/0328998 A1 | 11/2016 | Nita et al. |
| 2016/0338722 A1 | 11/2016 | Nita et al. |
| 2016/0367284 A1 | 12/2016 | Nita et al. |
| 2017/0065288 A1 | 3/2017 | Imai et al. |
| 2017/0128090 A1 | 5/2017 | Sarge |
| 2017/0265886 A1 | 9/2017 | Nita et al. |
| 2017/0354428 A1 | 12/2017 | Nita et al. |
| 2018/0042636 A1 | 2/2018 | Nita |
| 2018/0140321 A1 | 5/2018 | Deepa |
| 2018/0168668 A1 | 6/2018 | Zheng |
| 2018/0177515 A1 | 6/2018 | Boyle et al. |
| 2018/0197856 A1 | 7/2018 | Chou et al. |
| 2018/0221040 A1 | 8/2018 | Roll Hoye |
| 2018/0280005 A1 | 10/2018 | Parmentier |
| 2018/0280044 A1 | 10/2018 | Nita et al. |

FOREIGN PATENT DOCUMENTS

| | | |
|---|---|---|
| DE | 8910040 U1 | 12/1989 |
| DE | 3821836 A1 | 1/1990 |
| DE | 4042435 C2 | 2/1994 |
| DE | 10146011 A1 | 4/2003 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0472368 A2 | 2/1992 |
| EP | 0541249 A2 | 5/1993 |
| EP | 0820728 A2 | 1/1998 |
| EP | 1323481 A2 | 7/2003 |
| GB | 1106957 | 3/1968 |
| JP | H2-7150 U | 10/1988 |
| JP | 01-099547 | 4/1989 |
| JP | 6086822 A | 3/1994 |
| JP | 107500752 A | 1/1995 |
| JP | 7116260 A | 5/1995 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007512087 A | 5/2007 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |

(56) References Cited

FOREIGN PATENT DOCUMENTS

| WO | 9635469 | A1 | 11/1996 |
|----|---------|----|---------|
| WO | 9705739 | A1 | 2/1997 |
| WO | 9721462 | A1 | 6/1997 |
| WO | 9745078 | A1 | 12/1997 |
| WO | 9827874 | A1 | 7/1998 |
| WO | 9835721 | A2 | 8/1998 |
| WO | 9851224 | A2 | 11/1998 |
| WO | 9852637 | A1 | 11/1998 |
| WO | 9925412 | A2 | 5/1999 |
| WO | 0053341 | A1 | 9/2000 |
| WO | 0067830 | A1 | 11/2000 |
| WO | 02094103 | A1 | 11/2002 |
| WO | 03039381 | A1 | 5/2003 |
| WO | 2004012609 | A1 | 2/2004 |
| WO | 2004093736 | A2 | 11/2004 |
| WO | 2004112888 | A2 | 12/2004 |
| WO | 2005053769 | A2 | 6/2005 |
| WO | 2005112770 | A1 | 12/2005 |
| WO | 2006049593 | A1 | 5/2006 |
| WO | 2013109269 | A1 | 7/2013 |
| WO | 2014022716 | A2 | 2/2014 |
| WO | 2014105754 | A1 | 7/2014 |
| WO | 2014106847 | A1 | 7/2014 |
| WO | 2018097856 | A1 | 5/2018 |
| WO | 20180187159 | A1 | 10/2018 |

OTHER PUBLICATIONS

Sehgal, et al., Ultrasound-Assisted Thrombolysis, Investigative Radiology, 1993, vol. 28, Issue 10, pp. 939-943.
Siegel, et al., "In Vivo Ultrasound Arterial Recanalization of Atherosclerotic Total Occlusions", Journal of the American College of Cardiology, Feb. 1990, vol. 15, No. 2, pp. 345-351.
"What is Electron Beam Curing?" downloaded from web on Nov. 14, 2002, 4 pages total. <http://www.ms.oml.gov/researchgroups/composites/new%20orccmt%20pages/pages/ebwha>.
EP Extended Search Report dated Aug. 13, 2009; Application 04710537.5-1269, 5 pages.
Extended European Search Report dated Mar. 5, 2012 for European Application No. 12153606.4-1269.
Margaret Fyfe et al., Mast cell degranulation and increased vascular permeability induced by therapeutic' ultrasound in the rate ankle joint, Br. J. exp. Path., 1984, vol. 65, pp. 671-676.
"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.
Paul Yock et al., Catheter-Based Ultrasound Thrombolysis Shake, Rattle, and Repertuse, https://doi.org/10.1161/01.CIR.95.6.1360 Circulation. 1997;95:1360-1362 Originally published Mar. 18, 1997.
Noone, D.: Experimental and Numerical Investigation of Wire Waveguides for Therapeutic Ultrasound Angioplasty. M.Eng. Dublin City University. 2008.
Definition of the term "connected", retrieved on Sep. 21, 2013. <www.thefreedictionary.com/connected> 1 page total.
Supplemental European Search Report dated Nov. 5, 2009 for European Application No. EP03766931.
International Search Report dated Oct. 28, 2003 for PCT Application No. PCT/US2003/023468.
Extended European Search Report dated Mar. 22, 2012 for European Application No. EP11188799.
International Search Report dated Dec. 23, 2005 for PCT Application No. PCT/US2004/019378.
Extended European Search Report for Patent Application No. 06718204.8, dated May 30, 2012.
International Search Report dated Aug. 1, 2013 for PCT Application No. PCT/US2013/053306.
International Preliminary Report dated Aug. 1, 2013 for PCT Application No. PCT/US2013/053306.
Written Opinion dated Aug. 1, 2013 for PCT Application No. PCT/US2013/053306.
Supplemental European Search Report dated Apr. 29, 2009 for European Application No. EP 04711207.3.
Office Action dated Aug. 3, 2010 from Japanese Application No. 2006-517355 filed on Jun. 16, 2004.
Office Action dated Jan. 26, 2010 from Japanese Application No. 2006-517355 filed on Jun. 16, 2004.
International Preliminary Report and Written Opinion dated Aug. 1,2017 for PCT Application No. PCT/US2017/030675.
International Preliminary Report and Written Opinion dated Feb. 6, 2018 for PCT Application No. PCT/US2018/017022.
Calhoun et al., "Electron-Beam Systems for Medical Device Sterilization", downloaded from web on Oct. 8, 2002 <http://www.devicelink.com/mpb/archive/97/07/002.html> 7 pages total.
Definition of the term "coupled", retrieved on May 18, 2013. <http://www.merriam-webster.com/dictionary/couple> 1 page total.
"E-Beam Theory" RDI-IBA Technology Group, downloaded from web on Oct. 8, 2002 <http://www.e-beamrdi/EbeamTheory.htm> 2 pages total.
Office Action dated May 20, 2010 from Japanese Application No. 2006-541200 filed on Oct. 25, 2004.
Office Action dated Oct. 11, 2012 from Japanese Application No. 2010-181956.

* cited by examiner

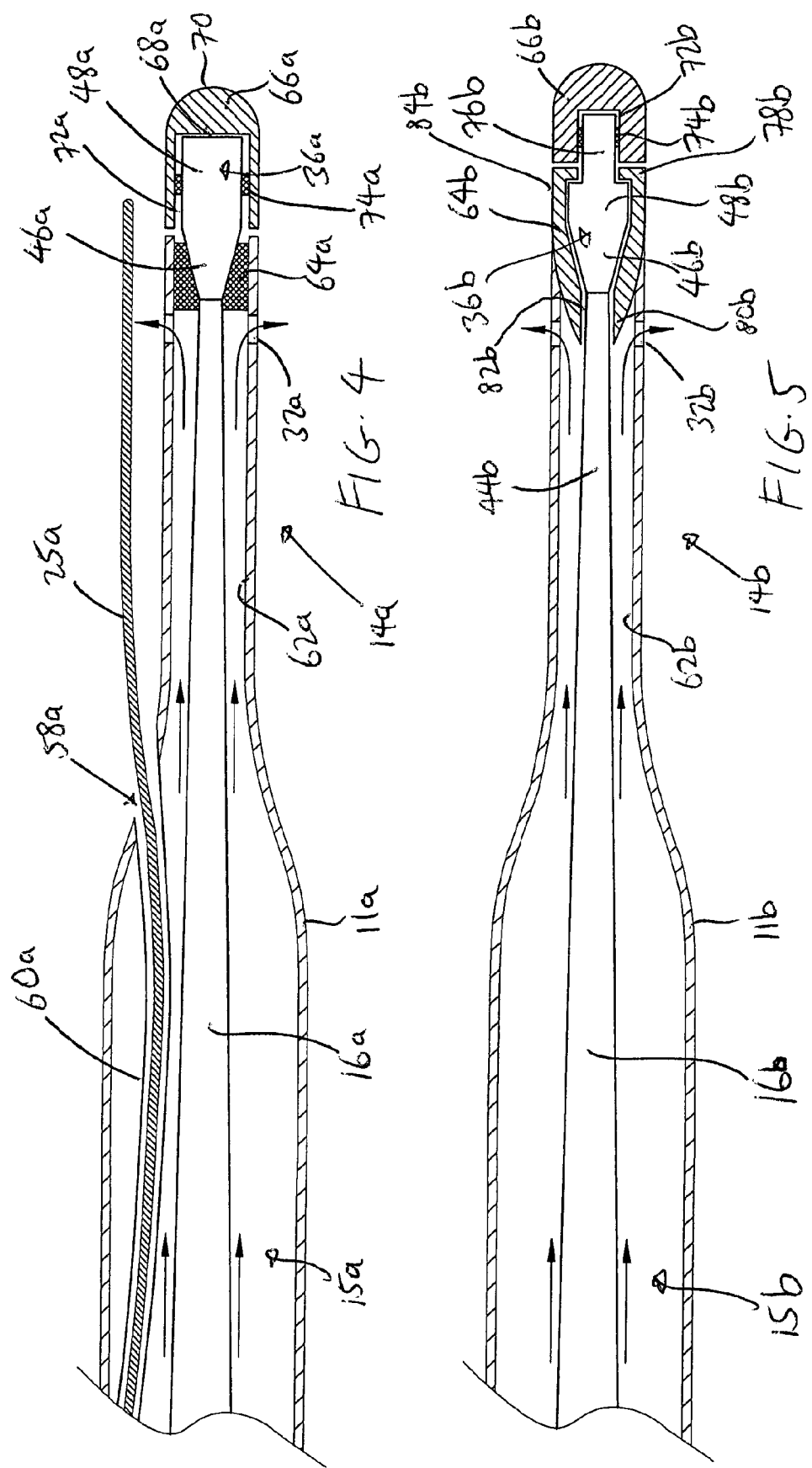

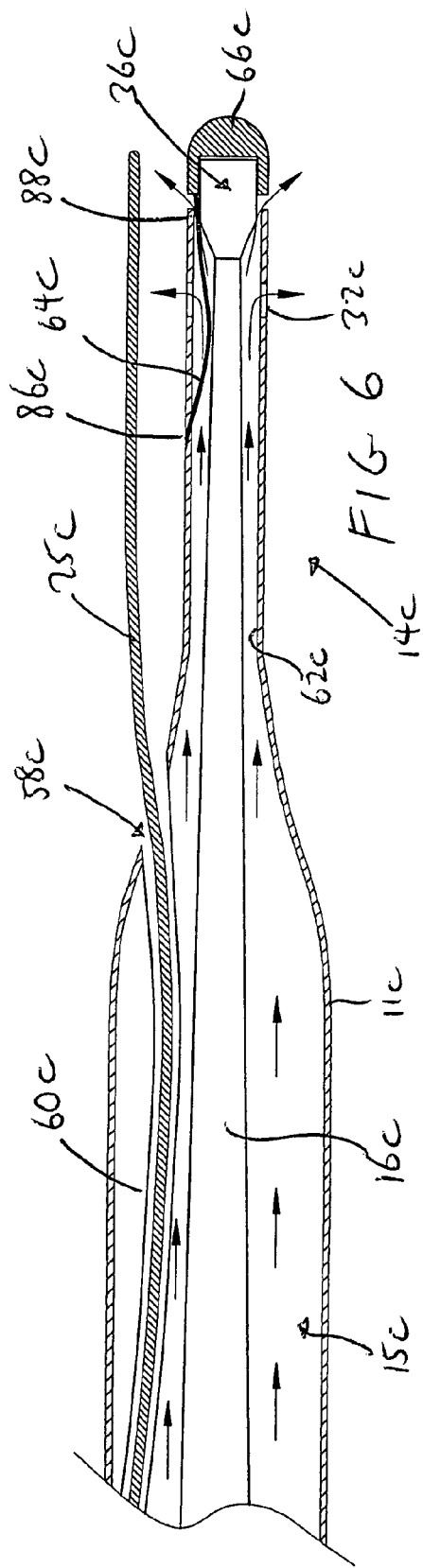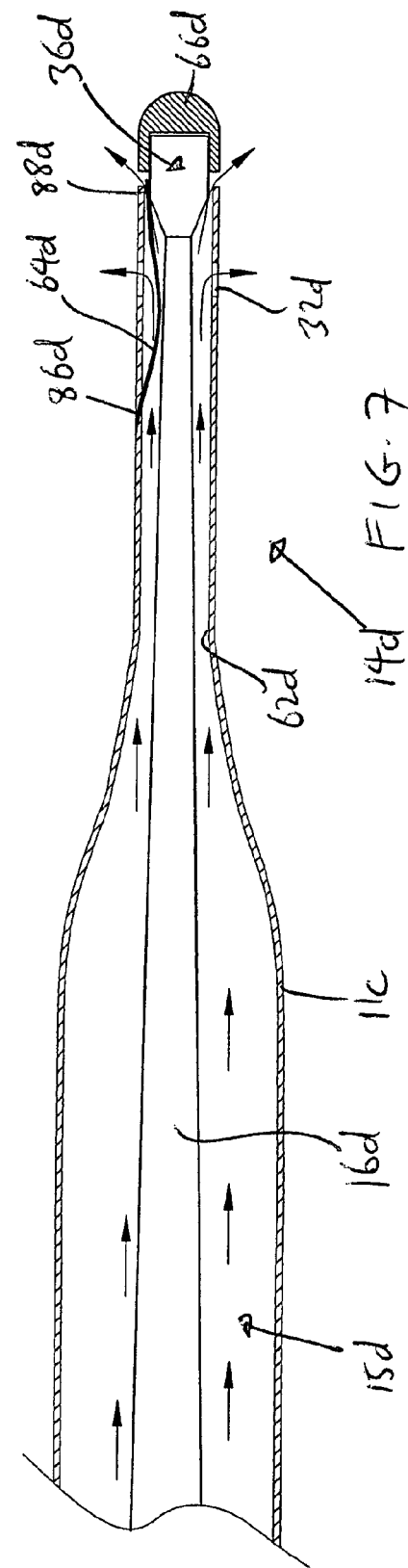

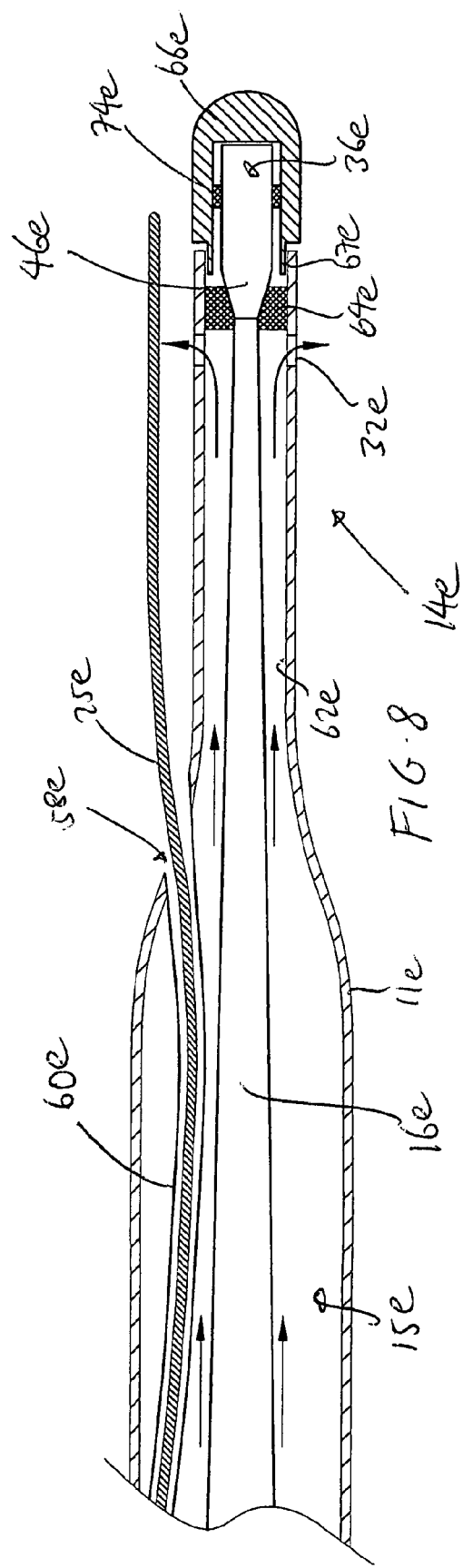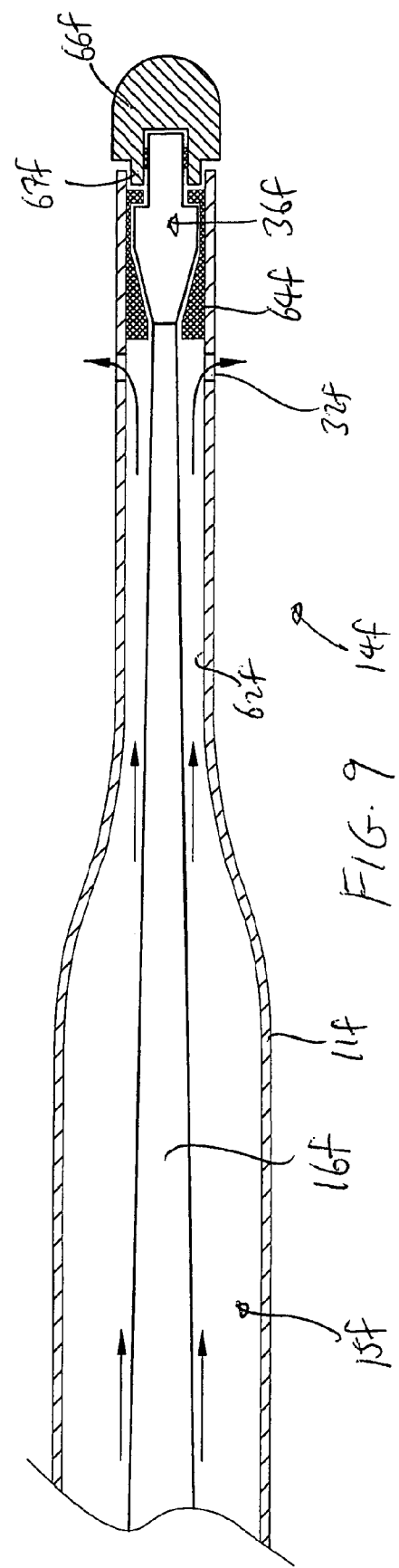

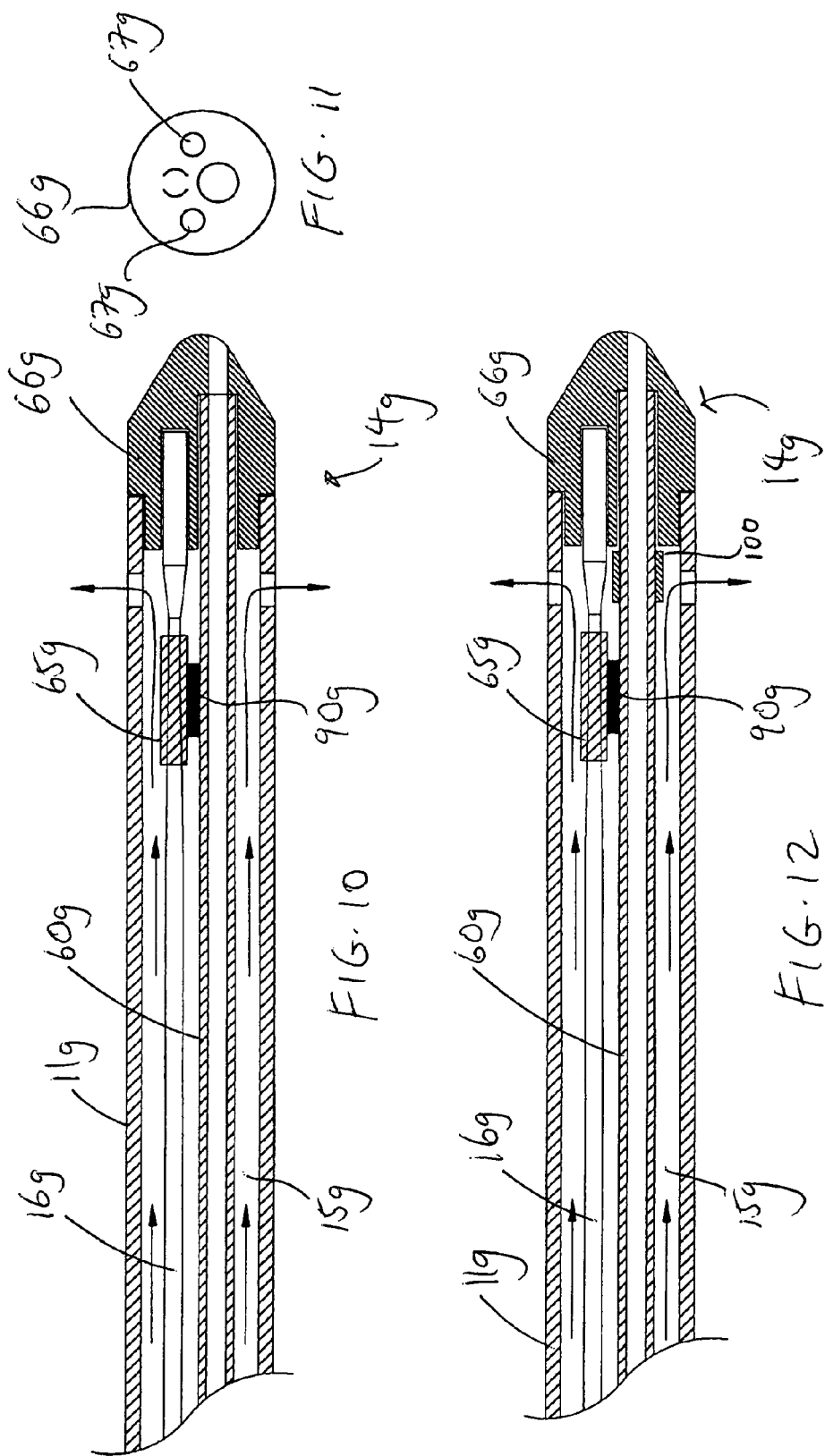

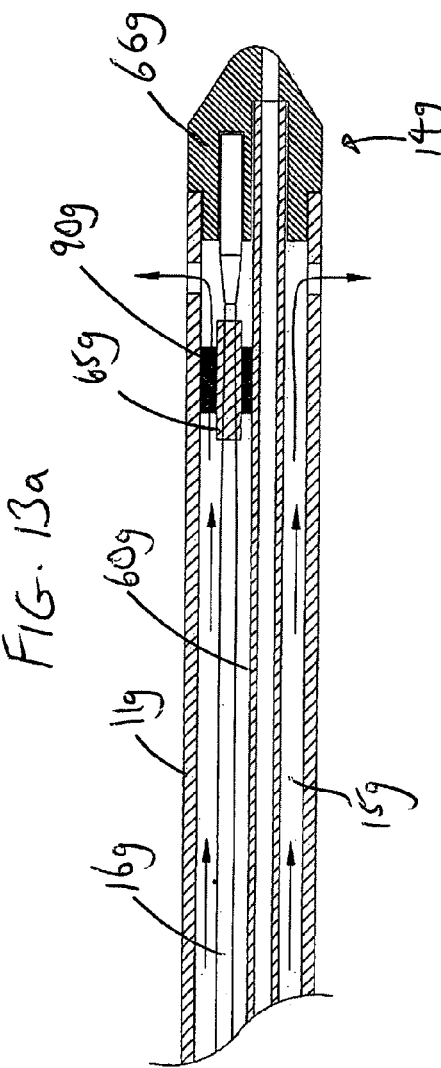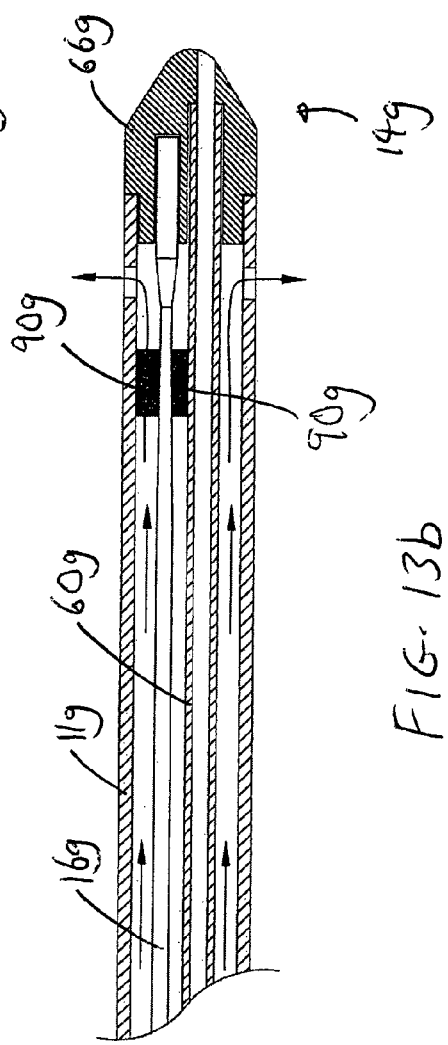

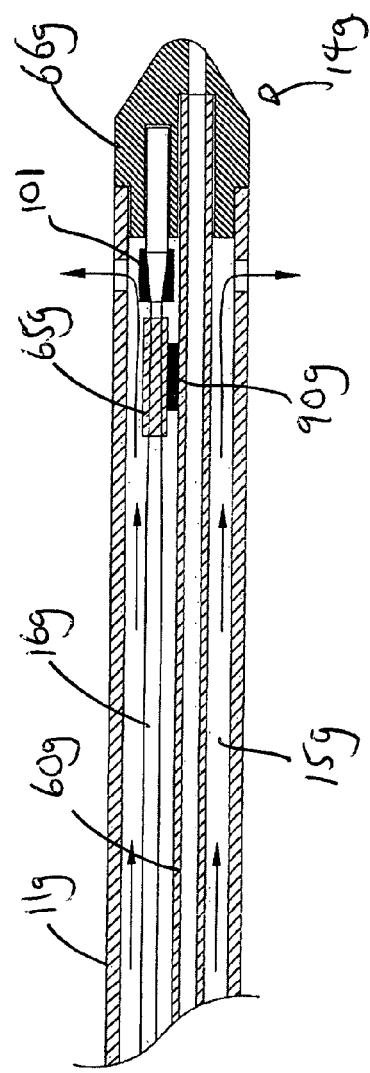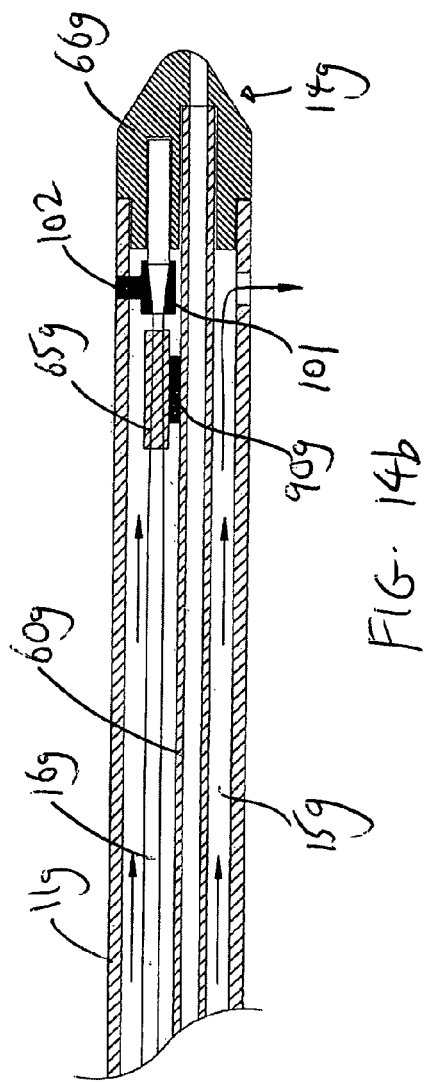

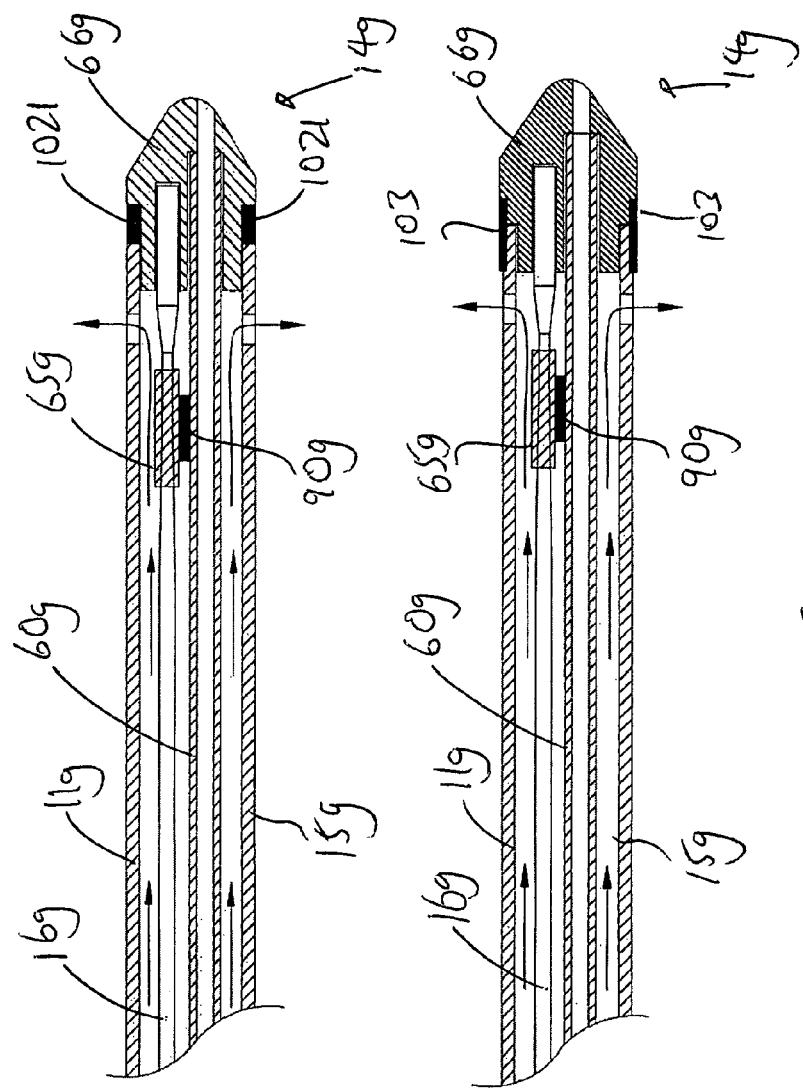

ULTRASOUND CATHETER HAVING PROTECTIVE FEATURE AGAINST BREAKAGE

CROSS-REFERENCE TO RELATED APPLICATIONS

This application is a continuation of U.S. patent application Ser. No. 13/919,739, filed Jun. 17, 2013, now U.S. Pat. No. 9,955,994, which is a continuation-in-part of U.S. patent application Ser. No. 12/004,984, filed Dec. 21, 2007, now U.S. Pat. No. 8,496,669, which is a continuation-in-part of U.S. patent application Ser. No. 11/594,663, filed Nov. 7, 2006, now U.S. Pat. No. 8,133,236, and a continuation-in-part of U.S. patent application Ser. No. 11/879,170, filed Jul. 16, 2007, now U.S. Pat. No. 8,506,519, which is a continuation-in-part of U.S. patent application Ser. No. 11/711,970, filed Feb. 27, 2007, now abandoned, which is a continuation-in-part of U.S. application Ser. No. 10/251,227, filed on Sep. 20, 2002, now U.S. Pat. No. 6,702,748 and a continuation of U.S. patent application Ser. No. 10/601,245, filed on Jun. 20, 2003, now abandoned, which is a continuation-in-part of U.S. patent application Ser. No. 10/211,418, filed on Aug. 2, 2002, now U.S. Pat. No. 6,855,123, all of which are hereby expressly incorporated by reference in their entirety.

BACKGROUND

Field

The present invention pertains to medical equipment, and more particularly, to a therapeutic ultrasound system for ablating obstructions within tubular anatomical structures such as blood vessels. The ultrasound system includes a protective feature that minimizes the introduction of debris into the patient's vasculature if the ultrasound transmission member were to break, fracture or become dislodged during a medical procedure.

Description of the Prior Art

A number of ultrasound systems and devices have heretofore been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, requires the use of relatively small diameter ultrasound catheters which are sufficiently small and flexible to undergo transluminal advancement through the tortuous vasculature of the aortic arch and coronary tree. However, because of its small diameter, the ultrasound transmission member which extends through such catheters is particularly susceptible to losses in the transmitted ultrasound energy, and breakage.

Breakage of ultrasound transmission members often occurs near the proximal end thereof, generally at the coupling between the ultrasound catheter coupling and the ultrasound transducer. This is believed to be because energy concentrations and stresses are highest at these points. Thus, any external forces applied to the ultrasound transmission member in this region may result in stresses exceeding the elastic limit of the ultrasound transmission member.

Breakage of ultrasound transmission members can also occur near the distal end thereof, generally at the area of the smallest cross-section. To minimize breakage of the ultrasound transmission wire at the distal end, a smaller distal tip with less mass or a tip made of polymer or a lower density metal may be utilized to further reduce stress at the distal in on the transmission wire. It is important that any debris resulting from the breakage of the ultrasound transmission member not be allowed to be introduced into a patient's vasculature during a medical procedure.

Thus, there still exists a need to further improve efficacy of the ultrasound systems and protect against breakage of the ultrasound transmission member during a medical procedure.

SUMMARY

It is an object of the present invention to provide an ultrasound catheter system with a protective feature that prevents or minimizes the introduction of debris into the patient's vasculature if the ultrasound transmission member were to break or fracture during a medical procedure.

In order to accomplish the objects of the present invention, there is provided an ultrasound catheter having an elongate flexible catheter body having a lumen extending longitudinally therethrough, and an ultrasound transmission member extending longitudinally through the lumen of the catheter body. The ultrasound transmission member has a proximal end that is coupled to a separate ultrasound generating device, and a distal end that terminates at the distal end of the catheter body. The ultrasound transmission member is directly attached to the guidewire tube and/or the catheter body, and such attachment can be accomplished using a direct attachment or via an attachment member. A radiopaque marker or sleeve can also be positioned on the distal end of the ultrasound catheter to improve its visibility.

BRIEF DESCRIPTION OF THE DRAWINGS

FIGS. 4-9 are cross-sectional views of the distal end of various ultrasound catheters that can be used with the system of FIG. 1 according to different embodiments thereof.

FIG. 10 illustrates the distal end of an ultrasound catheter according to another embodiment of the present invention that can be used with the system of FIG. 1, where the ultrasound transmission member is attached to the guidewire tube.

FIG. 11 is a front view of the distal end of the catheter of FIG. 10.

FIG. 12 illustrates a modification that can be made to the ultrasound catheter of FIG. 10 with a radiopaque marker located on the distal portion of the guidewire lumen.

FIGS. 13a and 13b illustrate a modification that can be made to the ultrasound catheter of FIG. 10 with the ultrasound transmission member attached to the guidewire tube and the catheter body.

FIGS. 14a and 14b illustrate a modification that can be made to the ultrasound catheter of FIG. 10 with a radiopaque marker located on the distal portion of the ultrasound transmission member.

FIGS. 15a and 15b illustrate a modification that can be made to the ultrasound catheter of FIG. 10 with a radiopaque marker positioned on the distal tip and a radiopaque marker positioned partially on the catheter body and partially on the distal tip.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
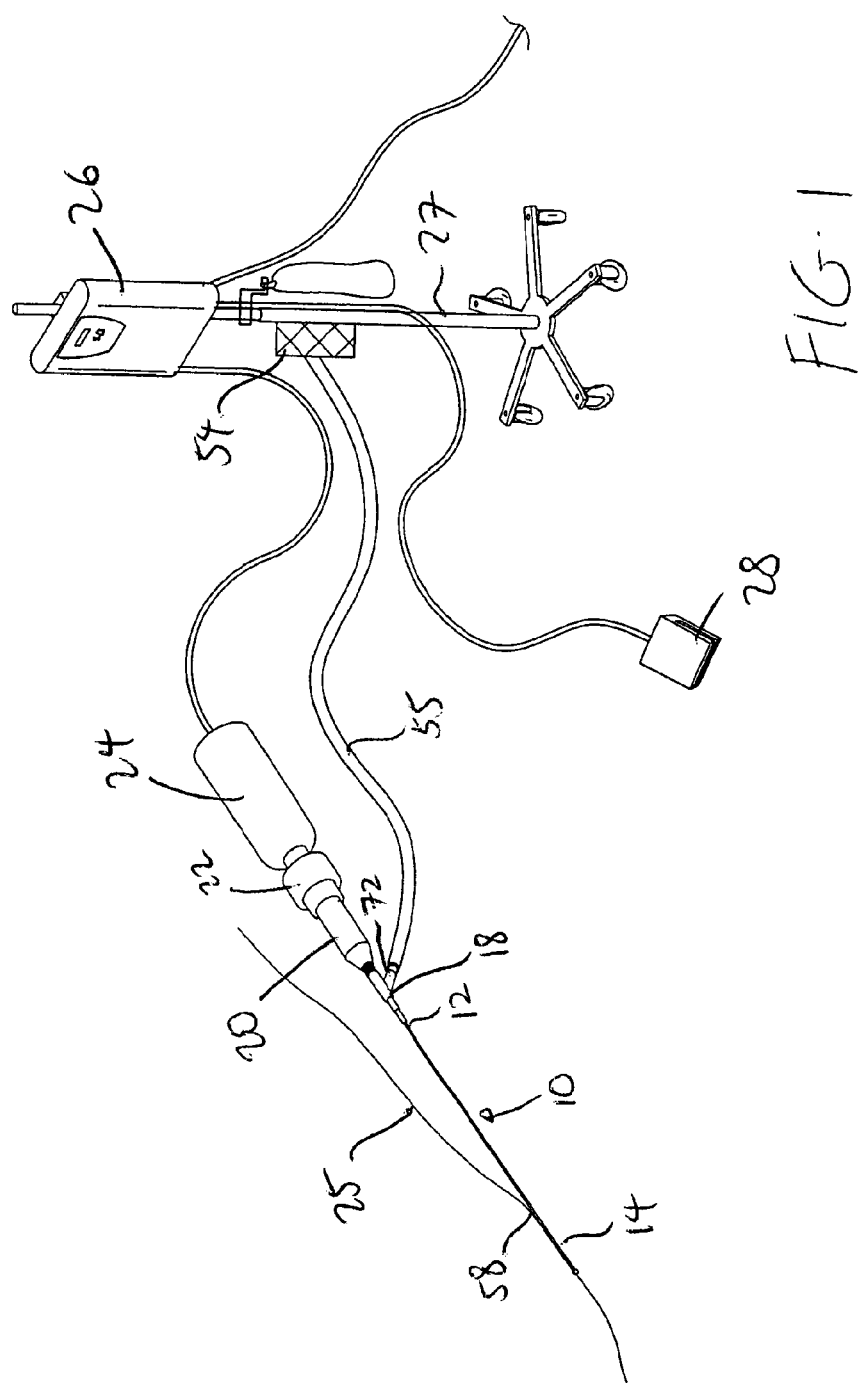
FIG. 1 is a perspective view of an ultrasound system according to the present invention.
Figure 2:
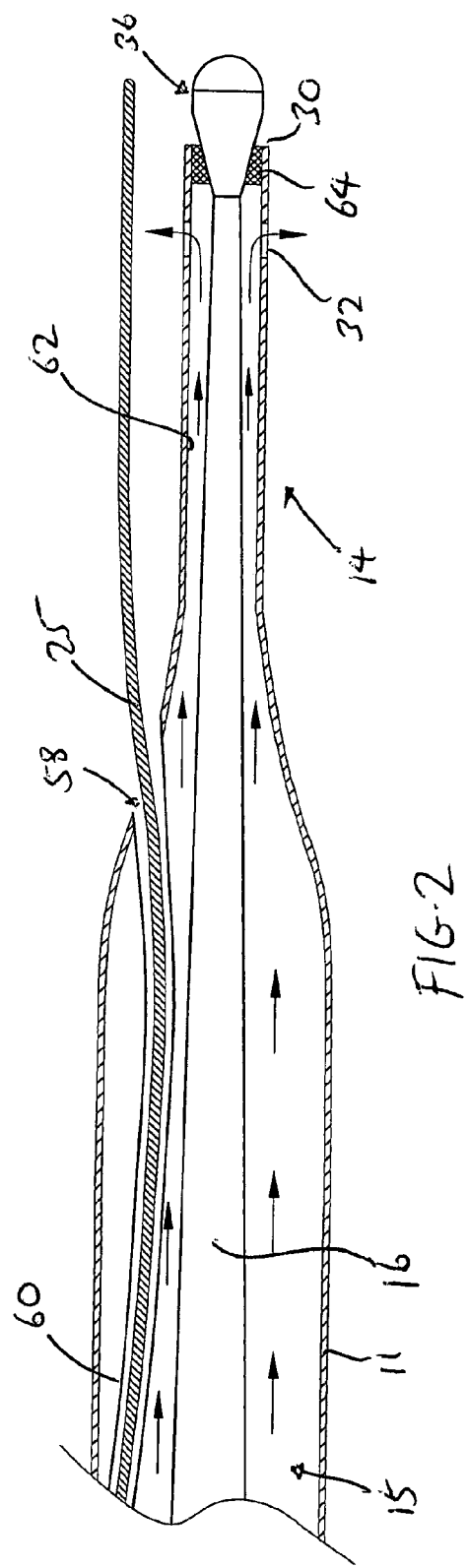
FIG. 2 is a cross-sectional view of the distal end of an ultrasound catheter that can be used with the system of FIG. 1 according to one embodiment thereof.

FIG. 1 illustrates an ultrasound system according to the present invention for use in ablating and removing occlusive material inside the vessel of an animal or human. Referring to FIGS. 1 and 2, the ultrasound system includes an ultrasound catheter device 10 which has an elongate catheter body 11 having a proximal end 12, a distal end 14, and defining at least one lumen 15 extending longitudinally therethrough. The ultrasound catheter device 10 is operatively coupled at its proximal end 12, by way of a Y-connector 18, a catheter knob 20, and a slide collar 22, to an ultrasound transducer 24. The ultrasound transducer 24 is connected to a signal generator 26, which can be provided with a foot actuated on-off switch 28. The signal generator 26 can be supported by an IV pole 27. When the on-off switch 28 is depressed, the signal generator 26 sends an electrical signal to the ultrasound transducer 24, which converts the electrical signal to ultrasound energy. Such ultrasound energy subsequently passes through the catheter device 10 and is delivered to the distal end 14. A guidewire 25 may be utilized in conjunction with the catheter device 10, as will be more fully described below.

The catheter body 11 is formed of a flexible polymeric material such as nylon (Pebax™) manufactured by Atochimie, Cour be Voie, Hauts Ve-Sine, France. The flexible catheter body 11 is preferably in the form of an elongate tube having one or more lumens extending longitudinally therethrough. The catheter body 11 defines a main lumen 15. Extending longitudinally through the main lumen 15 is an elongate ultrasound transmission member 16 having a proximal end which is removably connectable to the ultrasound transducer 24 via a sonic connector (not shown) such that ultrasound energy will pass through the ultrasound transmission member 16. As such, when the foot actuated on-off switch 28 operatively connected to the ultrasound transducer 24 is depressed; ultrasound energy will pass through the ultrasound transmission member 16 to the distal end 14 of the catheter body 11.

A guidewire port 58 is provided in the catheter body 11 at any location along the catheter body 11. A guidewire lumen 60 extends from the guidewire port 58 through the main lumen 15 of the catheter body 11 in a manner that is concomitant to the length of the ultrasound transmission member 16. In one embodiment, the guidewire port 58 can be provided at a location that is closer to the proximal end 12 than to the distal end 14 of the catheter.

In one embodiment, the ultrasound transmission member 16 may be formed of any material capable of effectively transmitting the ultrasonic energy from the ultrasound transducer 24 to the distal end 14 of the ultrasound transmission member 16, and is preferably made from metal or metal alloys. It is possible to form all or a portion of the ultrasound transmission member 16 with one or more materials which exhibit super-elasticity. Such materials should preferably exhibit super-elasticity consistently within the range of temperatures normally encountered by the ultrasound transmission member 16 during operation of the catheter device 10. Specifically, all or part of the ultrasound transmission member 16 may be formed of one or more metal alloys known as "shape memory alloys". Examples of super-elastic metal alloys which are usable to form the ultrasound transmission member 16 of the present invention are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 16 of the present invention operates, any and all of which super-elastic metal alloys may be usable to form the super-elastic ultrasound transmission member 16.

The frontal portion of the Y-connector 18 is connected to the proximal end 12 of the catheter 10 using techniques that are well-known in the catheter art. An injection pump 54 or IV bag (not shown) or syringe (not shown) can be connected, by way of an infusion tube 55, to an infusion port or sidearm 72 of the Y-connector 18 (see FIG. 1). The injection pump can be used to infuse coolant fluid into and/or through the main lumen 15 of the catheter 10, with the coolant fluid exiting via irrigation outlets 32 (see FIG. 2) provided adjacent the distal end 14 of the catheter 10. Such flow of coolant fluid may be utilized to prevent overheating of the ultrasound transmission member 16 extending longitudinally through the main lumen 15. Such flow of the coolant fluid through the main lumen 15 of the catheter 10 also serves to bathe the outer surface of the ultrasound transmission member 16, thereby providing for an equilibration of temperature between the coolant fluid and the ultrasound transmission member 16. Thus, the temperature and/or flow rate of coolant fluid may be adjusted to provide adequate cooling and/or other temperature control of the ultrasound transmission member 16. The irrigation fluid can include a pharmacological agent and/or microbubbles.

In addition to the foregoing, the injection pump 54 or syringe may be utilized to infuse a radiographic contrast medium into the catheter 10 for purposes of imaging. Examples of iodinated radiographic contrast media which may be selectively infused into the catheter 10 via the injection pump 54 are commercially available as Angiovist 370 from Berlex Labs, Wayne, N.J. and Hexabrix from Malinkrodt, St. Louis, Mo.

The proximal end of the Y-connector 18 is attached to the distal end of the catheter knob 20 by threadably engaging the proximal end of the Y-connector 18 inside a threaded distal bore (not shown) at the distal end of the catheter knob 20.

The proximal end of the ultrasound transmission member 16 is attached to a sonic connector (not shown) which is configured to effect operative and removable attachment of the proximal end of the ultrasound transmission member 16 to the horn of the ultrasound transducer 24. The sonic connector is preferably configured and constructed to permit passage of ultrasound energy through the ultrasound transmission member 16 with minimal lateral side-to-side movement of the ultrasound transmission member 16 while, at the same time, permitting unrestricted longitudinal forward/backward vibration or movement of the ultrasound transmission member 16. Examples of ultrasound transducers, sonic connectors and their connections are illustrated in U.S. Pat. Nos. 6,702,748, 6,855,123, 6,942,620 and 6,942,677, whose disclosures are incorporated by this reference as though set forth fully herein.

Figure 3:
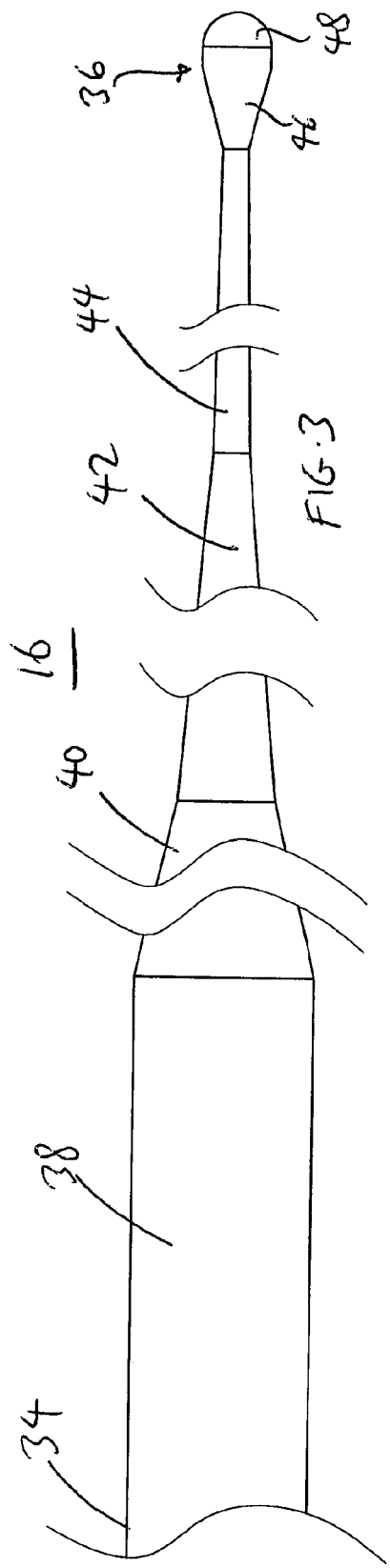
FIG. 3 is a side sectional view of an ultrasound transmission member that can be used with the system of FIG. 1.

Referring to FIGS. 2 and 3, the ultrasound transmission member 16 can have progressively tapered regions extending from the proximal end 34 thereof to the distal tip 36 thereof. For example, the proximal-most region 38 can have a constant diameter which is the greatest diameter along the length of the ultrasound transmission member 16. The region 38 transitions at its distal end to a first tapered region 40 which gradually decreases in diameter to its distal end to a second tapered region 42, which gradually decreases in diameter to its distal end to a third tapered region 44, which gradually decreases in diameter to its distal end to the distal tip 36. Each tapered region 40, 42, 44 can have a continuous taper, and be tapered to different degrees, such that the region 40 has a greater taper than the region 42, which in turn has a greater taper than the region 44. The distal-most part of the region 44 can have the smallest diameter along the entire ultrasound transmission member 16. The continuously decreasing tapering from the proximal to the distal direction shown in FIG. 3 allows for improved ultrasound energy propagation. The distal tip 36 can have a proximal section 46 which gradually increases in diameter until it reaches the proximal end of a distal section 48. The distal section 48 can have a bulbous configuration having a rounded or curved distal-most end that is adapted to contact the obstruction for ablation thereof. Thus, the distal tip 36 can have an enlarged size when compared to the rest of the ultrasound transmission member 16 so that the distal tip 36 can function as the distal head for the catheter In the embodiment shown in FIG. 2, the distal end 14 of the catheter body 11 has an opening 30, and the distal tip 36 of the ultrasound transmission member 16 is secured to the inner wall 62 of the main lumen 15 of the catheter body 11 adjacent the opening 30. The securement can be accomplished by an attachment mechanism 64 (which can be glue, welding or fusing) at the location of the proximal section 46 and the inner wall 62, so that part of the proximal section 46 is received inside the main lumen 15 and with the distal section 48 of the distal tip 36 extending outside the main lumen 15 of the catheter body 11. The opening 30 of the catheter body 11 is closed by the connection of the distal tip 36 to the catheter body 11. The construction shown in FIG. 2 directly attaches the ultrasound transmission member 16 to the catheter body 11 (via the attachment mechanism 64), which provides additional protection if the ultrasound transmission member 16 experiences breakage. In particular, if the ultrasound transmission member 16 fractures, breaks or splinters, the distal tip 36 will still remain secured to the catheter body 11 via the attachment device 64, and will not become dislodged from the catheter body 11. Thus, the embodiment of FIG. 2 does not employ a separate distal head for the catheter 10, but instead utilizes the distal tip 36 of the ultrasound transmission member 16 as a distal head which is secured directly to the distal end of the catheter body 11.

FIGS. 4-5 illustrate two different embodiments of a distal end of the catheter 10 which utilize the same principles and general construction as in FIG. 2, except that a distal cap is secured to the distal tip of the ultrasound transmission member. Therefore, the same numeral designations are used in FIGS. 2, 4 and 5 to designate the same or similar elements, except that an "a" and a "b" are added to the numeral designations in FIGS. 4 and 5, respectively. The differences between the embodiment of FIG. 2 and the embodiments in FIGS. 4 and 5 are described below.

The distal end 14a in FIG. 4 differs from the distal end 14 in FIG. 2 in that a protective cap 66a is secured to the distal section 48a of the distal tip 36a of the ultrasound transmission member 16a. The cap 66a can function as the tip of the catheter 10. The distal tip 36a itself has a different configuration from the distal tip 36 in FIG. 2 in that the distal section 48a is not bulbous or curved, but instead has a constant diameter that terminates distally at a flat distal end 68a. The cap 66a has a cylindrical configuration with an opened proximal end and a curved or bulbous distal end 70a. The distal section 48a of the distal tip 36a is received into the hollow bore 72a of the cap 66a via the opened proximal end of the cap 66a, and is secured to the cap 66a inside the bore 72a via an attachment device 74a (which can be the same as the attachment device 64). The cap 66a can be made of a radiopaque material to improve the visibility of the distal tip 36a.

In addition, instead of the attachment mechanism 64, the embodiments of FIGS. 4-5 provide an intermediate member 64a. The intermediate member 64a can be a cylindrical component that is positioned around the ultrasound transmission member 16a, and between the ultrasound transmission member 16a and the inner wall 62a of the catheter body 11a. The intermediate member 64a (as well as 64 and 64b) is preferably made from a material that does not effectively transfer or conduct heat, and which is easy to attach to the ultrasound transmission member 16a and the catheter body 11a. Examples of the material can include certain epoxies, polymers, plastics and rubber. According to one embodiment, the intermediate member 64a can be fused to the ultrasound transmission member 16a and the inner wall 62a. According to another embodiment, the intermediate member 64a can be bonded to the ultrasound transmission member 16a and the inner wall 62a. According to yet another embodiment, the intermediate member 64a can be fused to the ultrasound transmission member 16a and bonded to the inner wall 62a. The intermediate member 64a serves as a safety feature to hold the ultrasound transmission member 64a within the catheter body 11 in the event the ultrasound transmission member 16a experiences breakage at a location proximal to the intermediate member 64a. However, the intermediate member 64a will not be able to hold the distal tip 36a if the breakage occurs at the distal tip 36a.

The distal end 14b in FIG. 5 differs from the distal end 14a in FIG. 4 in the following ways. First, the guidewire port 58a, guidewire 25a, and guidewire lumen 60a have been omitted. Second, the distal tip 36b itself has a different configuration from the distal tip 36a in FIG. 4 in that a distal extension 76b extends distally from the distal section 48b. The distal extension 76b has a smaller constant diameter than the diameter of the enlarged distal section 48b, and the distal extension 76b is received into the hollow bore 72b of the cap 66b via the opened proximal end of the cap 66b, and is secured to the cap 66b inside the bore 72b via an attachment mechanism 74b (which can be the same as the attachment mechanism 64). The cap 66b can also be made of a radiopaque material to improve the visibility of the distal tip 36b.

Third, the intermediate member 64b in FIG. 5 has a different configuration as the intermediate member 64a. The intermediate member 64b has a generally conical configuration, having a wider diameter at its distal end 78b (which resembles the base of the cone) and a narrower diameter or dimension at its proximal end 80b (which resembles the narrowed tip of a cone). The hollow interior 82b of the intermediate member 64b has the greatest inner diameter adjacent its distal end 78b and decreases to its smallest inner diameter adjacent the proximal end 80b. This configuration for the intermediate member 64b allows the ultrasound transmission member 16b to be fitted and retained inside the hollow interior 82b without the need to directly attach the ultrasound transmission member 16b to the intermediate member 64b. Specifically, the sections 46b, 48b can be retained inside the hollow interior 82b, with the transition between the region 44b and the distal tip 36b (i.e., where the diameter of the ultrasound transmission member 16b is the smallest) received in the narrow opening of the proximal end 80b of the intermediate member 64b. In other words, the proximal end 80b overlaps a dimensional step (i.e., the transition between the region 44b and the distal tip 36b) on the ultrasound transmission member 16b. The distal extension 76b extends through another opening at the distal end 78b of the intermediate member 64b. To provide additional protection or safety, any or all of the sections 46b, 48b can also be bonded to the inner wall of the intermediate member 64b. The outer surface 84b of the intermediate member 64b may be attached to the opened distal end of the catheter body 11b by bonding, fusing or glue, and part of the intermediate member 64b extends beyond the distal end of the catheter body 11b.

Comparing the embodiments of FIGS. 4 and 5, the intermediate member 64b has an "overlapped" configuration, which provides added protection because the intermediate member 64b is seated on a dimensional step along the ultrasound transmission member 16b, and will always hold the proximal portions of the ultrasound transmission member 16b within the catheter body 11b as long as the intermediate member 64b is attached to the catheter body 11b.

FIG. 6 illustrates a modification that can be made to the embodiment in FIG. 4. The embodiments in FIGS. 4 and 6 utilize the same principles and general construction, so the same numeral designations are used in FIGS. 4 and 6 to designate the same or similar elements, except that a "c" is added to the numeral designations in FIG. 6.

In FIG. 6, the catheter body 11c, the guidewire port 58c, the guidewire lumen 60c, the guidewire 25c, the ultrasound transmission member 16c and the cap 66c can be the same as the catheter body 11a, the guidewire port 58a, the guidewire lumen 60a, the guidewire 25a, the ultrasound transmission member 16a and the cap 66a in FIG. 4. The primary difference is that the intermediate member 64a is now embodied in the form of an anchor wire 64c, which can be either a polymer or a metal. One end 86c of the wire 64c can be attached (e.g., by glue, fusing, bonding) to the inner wall 62c of the catheter body 11c, and the other end 88c of the wire 64c can be attached (e.g., by glue, bonding or welding) to the distal tip 36c and to the cap 66c. If the ultrasound transmission member 16c breaks at any location, then the ultrasound transmission member 16c will be retained inside the catheter body 11c.

FIG. 7 illustrates a modification that can be made to the embodiment in FIG. 6. Specifically, the embodiments in FIGS. 6 and 7 are the same except that the guidewire port 58c, the guidewire lumen 60c and the guidewire 25c are omitted in FIG. 7, and the anchor wire 64d is attached to the distal end of the ultrasound transmission member 16d but not attached to the cap 66d. Therefore, the same numeral designations are used in FIGS. 6 and 7 to designate the same elements, except that a "d" is added to the numeral designations in FIG. 7, and no further description of the elements in FIG. 7 is needed.

Attaching the anchor wire 64c or 64d to the cap 66c or 66d, or not attaching the anchor wire 64c or 64d to the cap 66c or 66d, provides different options. Attaching the anchor wire 64c to the cap 66c prevents dislodgement of the cap 66c or the distal tip 36c if the breakage occurs near or at the distal tip 36c. However, breakage at such locations is rare, so the embodiment in FIG. 7 (where the anchor wire 64d is not attached to the cap 66d) can also be employed.

FIG. 8 illustrates another modification that can be made to the embodiment in FIG. 4. Specifically, the embodiments in FIGS. 4 and 8 are the same, except that the proximal portion of the cap 66e has an annular edge 67e that extends into the interior of the catheter body 11e. Therefore, the same numeral designations are used in FIGS. 4 and 8 to designate the same elements, except that an "e" is added to the numeral designations in FIG. 8, and no further description of the elements in FIG. 8 is needed. The annular edge 67e is not attached to the catheter body 11e, and is maintained separate from the catheter body 11e. One benefit which is provided by extending a portion of the cap 66e into the catheter body 11e is that this arrangement provides a smooth and friendly transition between the distal cap 66e and the catheter body 11e. This smooth transition facilitates navigation of the distal end 14e through tortuous anatomy. Also, the non-affixed tip of the catheter body 11e can result in the improved transmission of ultrasound energy from the transducer to the distal end 14e.

FIG. 9 illustrates a modification that can be made to the embodiment in FIG. 5. Specifically, the embodiments in FIGS. 5 and 9 are the same except that the intermediate member 64f is completely retained inside the catheter body 11f, and the proximal portion of the cap 66f has an annular edge 67f that extends into the interior of the catheter body 11f. Therefore, the same numeral designations are used in FIGS. 5 and 9 to designate the same elements, except that an "f" is added to the numeral designations in FIG. 9, and no further description of the elements in FIG. 9 is needed.

A guidewire has been included in the embodiments of FIGS. 2, 4, 6 and 8, while the guidewire has been omitted in the embodiments of FIGS. 5, 7 and 9. Embodiments showing the use or omission of a guidewire are shown for reference only. The principles of the present invention may be applied to catheters that include, or not include, a guidewire. The use or omission of a guidewire depends upon the choice of the clinician, and is often dictated by the access difficulty or specific clinical situations. For example, if the target lesion is located on a straight portion of the vessel, use of a non-guidewire embodiment will be feasible and relatively easy. On the other hand, if the target lesion is located in a tortuous location of the vessel, then use of a guidewire embodiment will help the clinician to navigate the distal tip 36 to the location of the lesion.

FIGS. 10-11 illustrate a different embodiment of the present invention where the ultrasound transmission member is directly connected to the guidewire tube. Since the embodiment of FIGS. 10-11 utilize the similar principles and constructions as the other embodiments, the same numeral designations are used in FIG. 10 to designate the same elements as in the earlier embodiments, except that a "g" is added to the numeral designations. The ultrasound catheter has an elongate catheter body 11g, and at least one lumen 15g extending longitudinally therethrough. A guidewire lumen is defined by a guidewire tube 60g which extends through the lumen 15g inside the catheter body 11g and has a distal end that extends through a distal tip or cap 66g. The cap 66g has at least one irrigation outlet hole 67g that communicates with the lumen 15g. The ultrasound transmission member 16g extends longitudinally through the lumen 15g of the catheter body 11g, and its distal end is secured in a proximal bore of the cap 66g. The ultrasound transmission member 16g is attached adjacent its distal end to the guidewire tube 60g. The attachment can be accomplished by the direct use of glue, welding or fusing. Also, the attachment may be accomplished by using an attachment member 65g, which can be glued, welded or fused to the ultrasound transmission member 16g and guidewire tube 60g. The attachment member 65g can be tubular. The construction shown in FIG. 10 shows the ultrasound transmission member 16g attached to the guidewire tube 60g via the attachment member 65g (which can be a polymer sleeve) using any applicable glue 90g. The cap 66g and the ultrasound transmission member 16g may be made of the same or different materials connected together. Both these parts may also be manufactured entirely from a single piece of material without the need to separately connect each other.

FIG. 12 shows the catheter of FIG. 10 modified to include an additional radiopaque marker 100 attached to the distal portion of the guidewire tube 60g. If the cap 66g is very small or made of a polymer or a low density metal, these materials exhibit a relatively low visibility under fluoroscopy. In such a case, an additional radiopaque marker may be needed to improve visibility of the distal end 14g of the catheter. The radiopaque marker 100 may be placed around the guidewire tube 60g, or attached to the guidewire tube, or to the catheter body 11g (not shown), or to the ultrasound transmission member 16g (not shown), or both, using any applicable methods such as a glue or thermal fusing. The radiopaque marker 100 may also be positioned inside the distal end of the catheter body 11g (not shown) or inside the distal cap 66g (not shown). The radiopaque marker may be provided in the form of a tubular sleeve or coil (not shown). A radiopaque rod or wire (not shown) positioned inside the hole 67g may serve the same purpose as well. Such a sleeve, coil, rod or wire may be made of any radiopaque material including but not limited to platinum or gold.

FIG. 13a shows the catheter of FIG. 10 modified so that the distal end of the ultrasound transmission member 16g is attached to the guidewire tube 60g and the catheter body 11g via attachment member 65g using applicable glue 90g for further preventing or minimizing the introduction of debris into the patient's vasculature if the ultrasound transmission member 16g were to break or fracture during a medical procedure.

FIG. 13b shows the catheter of FIG. 10 modified so that the ultrasound transmission member 16g is directly attached to the guidewire tube 60g and the catheter body 11g using any applicable glue 90g, and eliminating the attachment member 65g as shown in the FIG. 13a.

FIG. 14a shows the catheter of FIG. 10 modified to include an additional radiopaque marker 101 positioned on the distal portion of the ultrasound transmission member 16g. Alternatively, the radiopaque marker 101 may be positioned freely on the ultrasound transmission member 16g and attached to the catheter body 11g using any applicable glue 120 as shown in FIG. 14b. The radiopaque marker 101 may be positioned freely or attached/affixed to the ultrasound transmission member 16g using any known technique, including but not limited to welding, soldering, fusing, glue or bonding.

FIG. 15a shows the catheter of FIG. 10 modified to include an additional radiopaque marker 1021 positioned solely on the cap 66g of the catheter 14g. Alternatively, a radiopaque marker 103 may be positioned partially on the cap 66g and partially on the catheter body 11g, as shown in FIG. 15b. The radiopaque marker 1021 may be positioned freely or attached to the cap 66g using known technique, such as welding, soldering, fusing, glue, or bonding. If the radiopaque marker 103 is partially located on the catheter body 11g and partially on the cap 66g, it can also be positioned freely or attached to one or both of these components.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A catheter comprising:
   a body having a lumen;
   an attachment disposed within the lumen, the attachment completely retained inside the lumen;
   a tube adapted to receive a guidewire attached to the body through the attachment;
   an ultrasound transmission member (UTM) disposed in the lumen and having a distal tip, wherein the attachment connects the tube to the UTM; and
   a cap disposed on the distal tip,
   wherein the attachment is proximal to the cap.

2. The catheter of claim 1 wherein the attachment irremovably attaches the UTM to the tube.

3. The catheter of claim 2 wherein the attachment is disposed around the UTM.

4. The catheter of claim 3 wherein the attachment comprises a sleeve.

5. The catheter of claim 4 wherein a proximal end of the attachment is distal of a proximal end of the body.

6. The catheter of claim 5 wherein the attachment is attached to the UTM, the tube, and the body.

7. The catheter of claim 6 wherein the tube is additionally attached to the distal tip or the cap.

8. The catheter of claim 1 wherein the UTM is adapted for connection to an ultrasound generator integral to the catheter.

9. The catheter of claim 8 wherein the attachment irremovably attaches the UTM to the tube.

10. The catheter of claim 9 wherein the attachment is disposed around the UTM.

11. The catheter of claim 10 wherein the attachment comprises a sleeve.

12. The catheter of claim 11 wherein a proximal end of the attachment is distal of a proximal end of the body.

13. The catheter of claim 12 wherein the attachment is attached to the UTM, the tube, and the body.

14. The catheter of claim 13 wherein a distal end of the tube attaches to the distal tip.

15. The catheter of claim 1 further comprising:
   the distal tip having a distal section; and
   the cap disposed directly on the distal section of the distal tip.

16. The catheter of claim 1 further comprising the cap having a cylindrical configuration, an open proximal end, and a protective cap distal end.

17. A catheter comprising:
   a body having a lumen;
   an attachment disposed within the lumen, the attachment completely retained inside the lumen, the attachment comprises a sleeve, the sleeve comprises an open distal end and an open proximal end;
   a tube adapted to receive a guidewire attached to the body through the attachment;

an ultrasound transmission member (UTM) disposed in the lumen and having a distal tip, wherein the attachment connects the tube to the UTM; and a cap disposed on the distal tip;

wherein the attachment irremovably attaches the UTM to the tube, the attachment is disposed around the UTM, the open distal end of the sleeve is proximal to the cap and the distal tip of the UTM.

* * * * *